United States Patent
Reichert et al.

(10) Patent No.: US 12,396,819 B2
(45) Date of Patent: Aug. 26, 2025

(54) STERILIZATION CONTAINER AND LATCH

(71) Applicant: Stryker Corporation, Kalamazoo, MI (US)

(72) Inventors: Daniel Reichert, Climax, MI (US); Benjamin Edinger, Grand Haven, MI (US); Anthony Sall, Zeeland, MI (US)

(73) Assignee: Stryker Corporation, Portage, MI (US)

( * ) Notice: Subject to any disclaimer, the term of this patent is extended or adjusted under 35 U.S.C. 154(b) by 196 days.

(21) Appl. No.: 18/139,178

(22) Filed: Apr. 25, 2023

(65) Prior Publication Data

US 2023/0338105 A1    Oct. 26, 2023

Related U.S. Application Data

(60) Provisional application No. 63/334,272, filed on Apr. 25, 2022.

(51) Int. Cl.
| | |
|---|---|
| *E05B 19/14* | (2006.01) |
| *A61B 50/30* | (2016.01) |
| *A61B 90/00* | (2016.01) |
| *E05B 65/52* | (2006.01) |

(52) U.S. Cl.
CPC ...... *A61B 50/30* (2016.02); *A61B 2090/0813* (2016.02)

(58) Field of Classification Search
CPC .......... Y10T 292/216; Y10T 292/0871; Y10T 292/0913; Y10T 292/0914; E05B 15/0086; E05B 65/52; E05B 65/5276; E05B 65/5246; E05C 19/14; Y10S 292/31

USPC ................................................... 292/256.69
See application file for complete search history.

(56) References Cited

U.S. PATENT DOCUMENTS

| | | | | |
|---|---|---|---|---|
| 3,584,906 A | * | 6/1971 | Budzyn | E05C 19/14 70/76 |
| 3,706,467 A | * | 12/1972 | Martin | E05C 19/14 292/DIG. 20 |
| 3,936,082 A | * | 2/1976 | Swanson | E05C 19/14 292/DIG. 31 |
| 4,181,333 A | * | 1/1980 | Stelma | E05C 19/14 292/DIG. 20 |
| 4,300,794 A | * | 11/1981 | Dunsmoor | E05C 19/14 292/DIG. 31 |
| D303,625 S | * | 9/1989 | Ryser | D8/336 |

(Continued)

FOREIGN PATENT DOCUMENTS

| | | | |
|---|---|---|---|
| CN | 116771209 A | * | 9/2023 |
| KR | 200403411 Y1 | * | 12/2005 |

(Continued)

*Primary Examiner* — Carlos Lugo
(74) *Attorney, Agent, or Firm* — Howard & Howard Attorneys PLLC

(57) ABSTRACT

A sterilization container for medical instruments comprising a base and a lid. A latch may be attached to the lid. The latch may include a mount body and a lever body pivotably coupled to the mount body such that the lever body and the mount body cooperate to define an interior having an opening. A deflector may be positioned within the interior and movable with the lever body. The deflector may include a hub portion supported, a wing portion extending from the hub portion to positioned adjacent to the opening of the interior such that when the lever body is in a secured position the wing portion prevents access to the interior through the opening.

18 Claims, 12 Drawing Sheets

(56) References Cited

U.S. PATENT DOCUMENTS

| | | | | |
|---|---|---|---|---|
| 4,915,913 | A * | 4/1990 | Williams | B65D 45/24 |
| | | | | 436/1 |
| 4,920,771 | A * | 5/1990 | Jiang | E05B 37/02 |
| | | | | 70/4 |
| 7,017,955 | B1 * | 3/2006 | Chiang | E05C 19/14 |
| | | | | 292/113 |
| 8,297,464 | B2 * | 10/2012 | Grenier | A45C 13/1084 |
| | | | | 220/314 |
| 10,434,206 | B2 | 10/2019 | Thomas et al. | |
| 11,504,204 | B2 | 11/2022 | Wissmann | |
| 2012/0080891 | A1 * | 4/2012 | Bravo | E05C 17/443 |
| | | | | 292/251.5 |

FOREIGN PATENT DOCUMENTS

| | | | | |
|---|---|---|---|---|
| WO | WO-2007095645 A2 * | 8/2007 | ........... | E05B 1/0092 |
| WO | 2020198666 A2 | 10/2020 | | |
| WO | WO-2022063588 A1 * | 3/2022 | ............. | E05C 19/14 |

\* cited by examiner

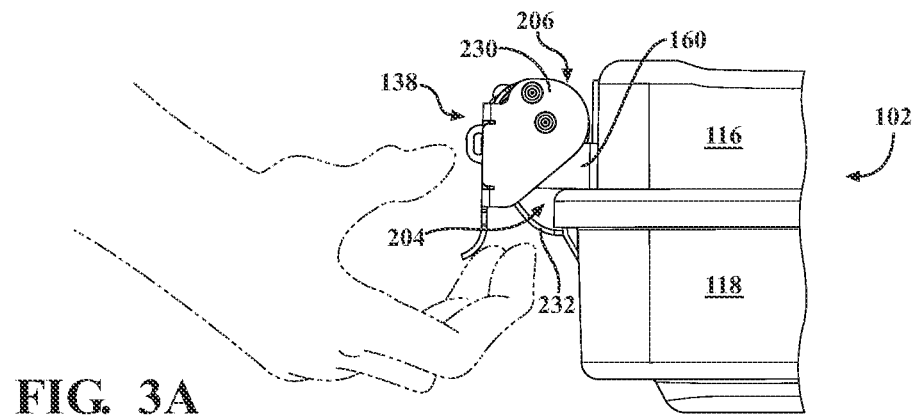
FIG. 3A
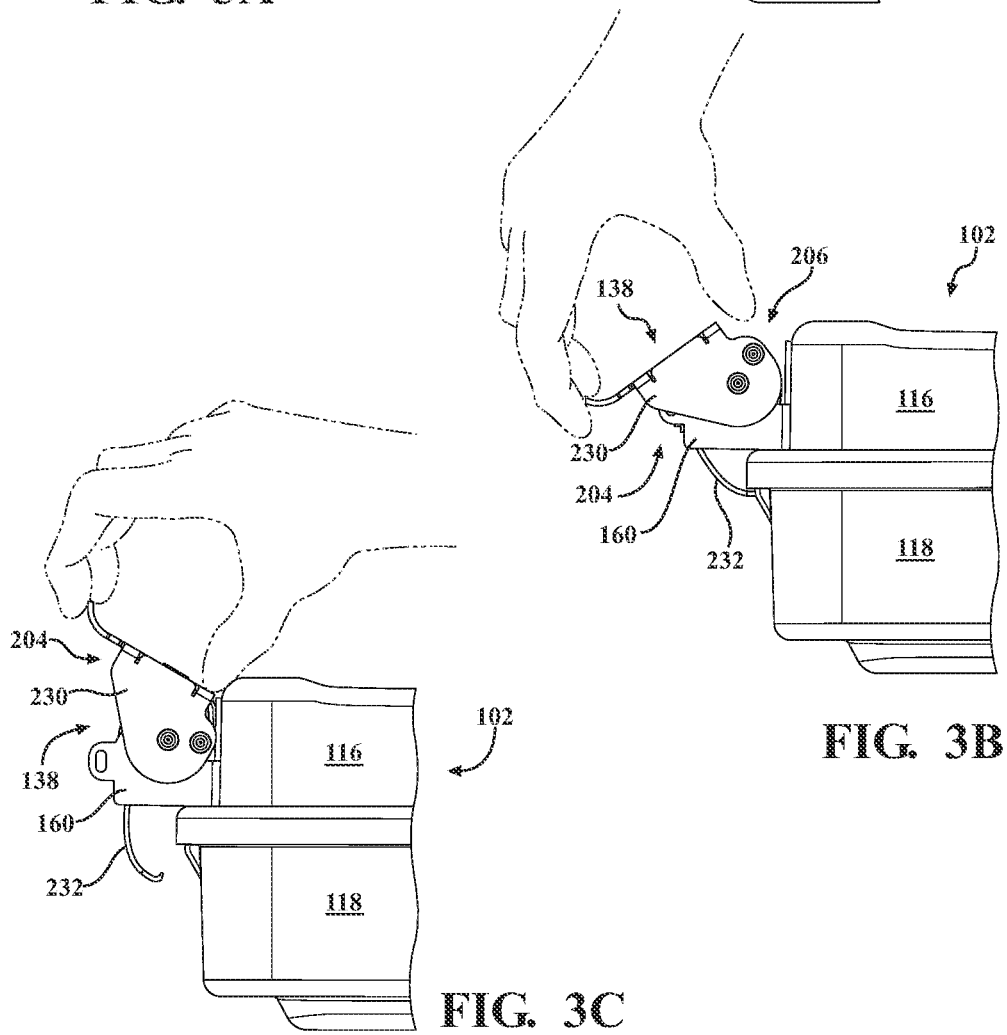
FIG. 3B
FIG. 3C

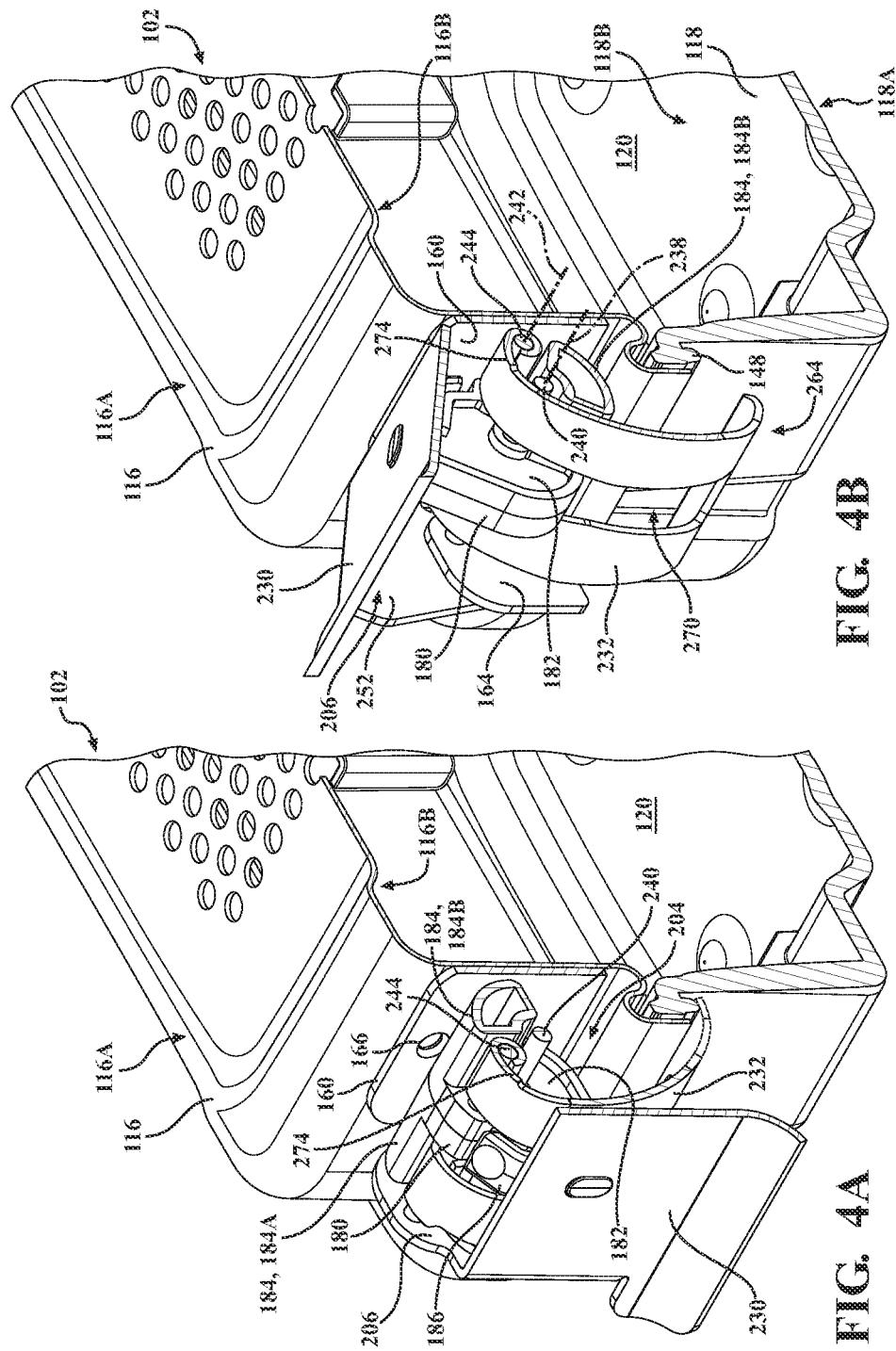

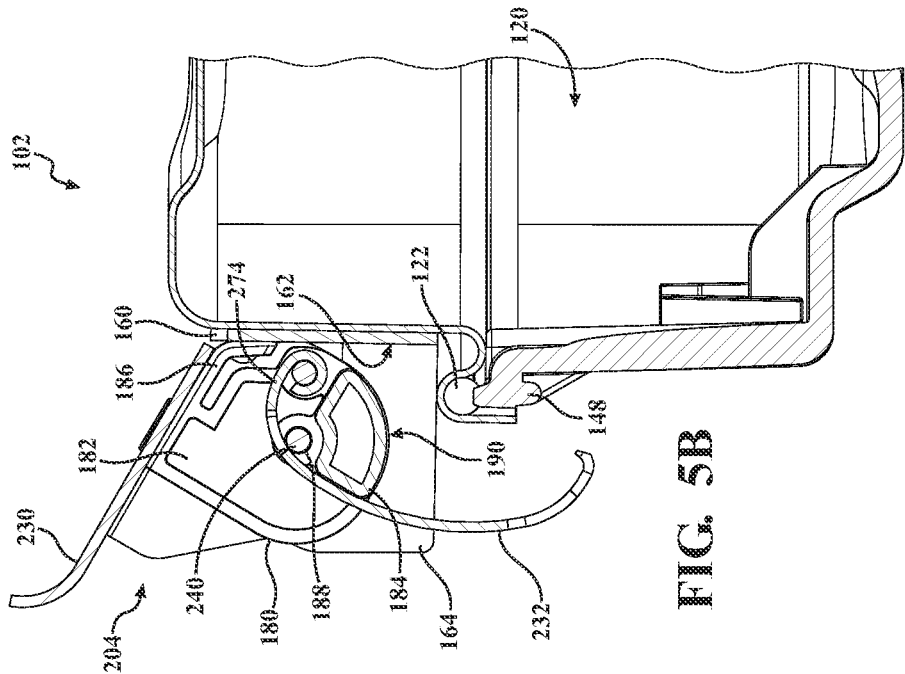
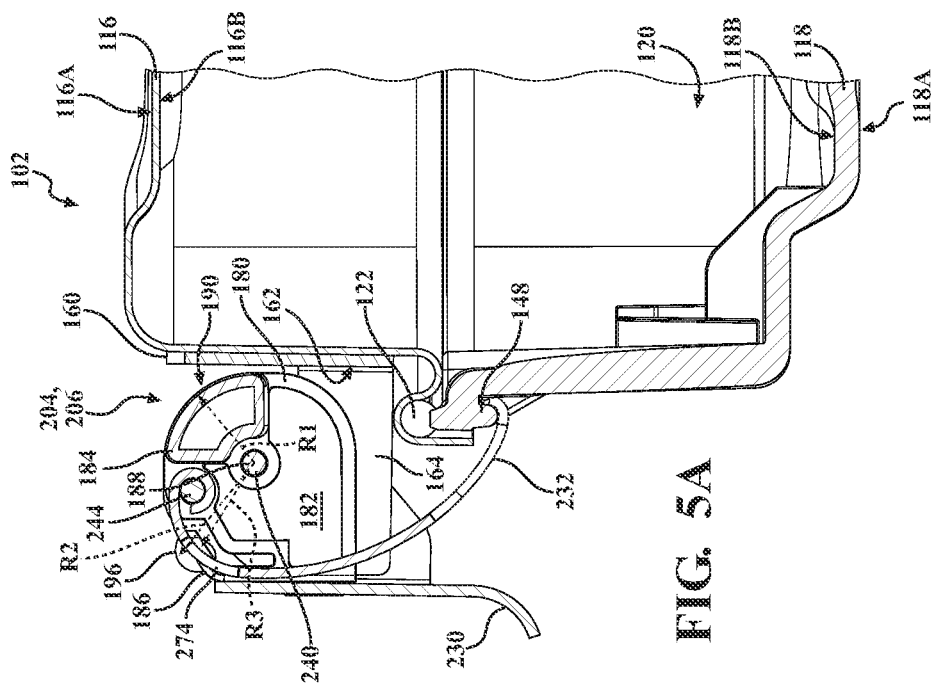

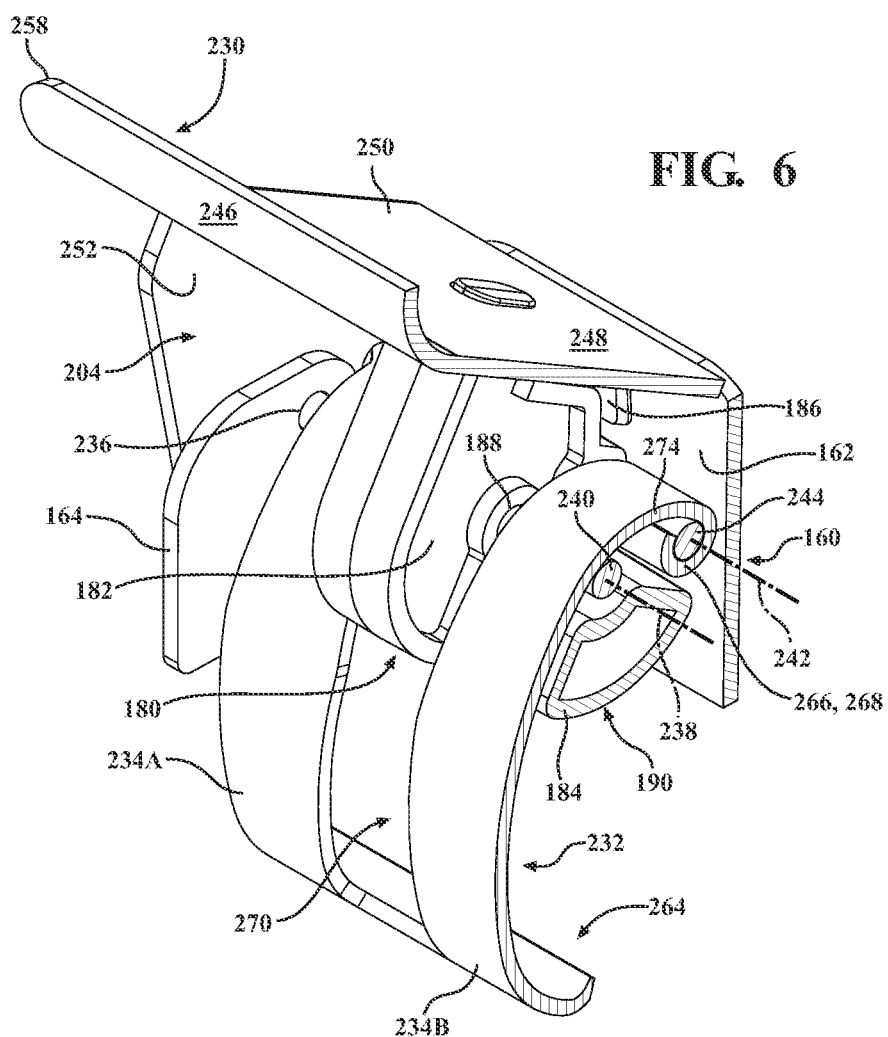

STERILIZATION CONTAINER AND LATCH

CROSS-REFERENCE TO RELATED APPLICATIONS

The subject patent application claims priority to, and all the benefits of, United States Provisional Patent Application No. 63/334,272, filed on Apr. 25, 2022, the entire contents of which are incorporated by reference herein.

BACKGROUND

Prior to a medical or surgical procedure, the tools and instruments to be utilized during the procedure are sterilized in order to avoid the spread of contaminants. In some cases, the instruments are sterilized inside a durable and reusable sterilization container, which is then used to transport the sterilized instruments from the sterilizing equipment to a treatment location, such as an operating room. Transporting instruments in this manner allows their sterility to be maintained until the moment the tool is removed from the container. Because the exterior of the sterilization container is non-sterile following transportation to the treatment location, it is desirable to minimize contact with the container when the container is opened.

SUMMARY

In one aspect, a sterilization container for medical instruments. The sterilization container may comprise a base and a lid configured for engaging the base. The base and the lid may collectively define a volume for receiving medical instruments. The sterilization container may further comprise a latch, which may be attached to one of the base and the lid. The latch may comprise a mount body including a back portion and two side portions, wherein the back portion is coupled to the lid or the base. The latch may further comprise a lever body including two side portions. The two side portions of the lever body may be pivotably coupled to the two side portions of the mount body such that the lever body is movable about a pivot axis between a secured position and an unsecured position. When the lever body is pivotably coupled to the two side portions of the mount body, the lever body and the mount body cooperate to define an interior and further define an opening of the interior when the lever body is in the secured position. The latch may further comprise a deflector positioned at least partially within the interior and movable with the lever body for concurrent movement about the pivot axis. The deflector may comprise a hub portion supported on the pivot axis and a wing portion extending from the hub portion to define an outer surface. The outer surface may be positioned adjacent to the opening of the interior when the lever body is in the secured position for preventing access to the interior through the opening. The deflector may further comprise a tab coupled to the hub portion and separate from the wing portion. The tab is configured to engage the mount body when the lever body is in the unsecured position for retaining the lever body in the unsecured position.

Any of the above aspects can be combined in full or in part. Any features of the above aspects can be combined in full or in part. Any of the above implementations for any aspect can be combined with any other aspect. Any of the above implementations can be combined with any other implementation whether for the same aspect or a different aspect.

BRIEF DESCRIPTION OF THE DRAWINGS

Advantages of the present disclosure will be readily appreciated as the same becomes better understood by reference to the following detailed description when considered in connection with the accompanying drawings.

FIG. 3A is a side view of a user interacting with the sterilization container with the latch shown in the secured position.

FIG. 3B is a side view of a user interacting with the sterilization container with the latch shown in an intermediate position.

FIG. 3C is a side view of a user interacting with the sterilization container with the latch shown in the unsecured position.

FIG. 4A is a cross-sectional perspective view of the sterilization container and the latch of FIG. 2A, with the latch shown in the secured position.

FIG. 4B is a cross-sectional perspective view of the sterilization container and the latch of FIG. 2B, with the latch shown in the unsecured position.

FIG. 5A is a cross-sectional perspective view of the sterilization container and the latch of FIG. 4A, with the latch shown in the secured position.

FIG. 5B is a cross-sectional perspective view of the sterilization container and the latch of FIG. 4B, with the latch shown in the unsecured position.

FIG. 6 is a cross-sectional perspective view of the latch of FIG. 4A.

DETAILED DESCRIPTION

Figure 1:
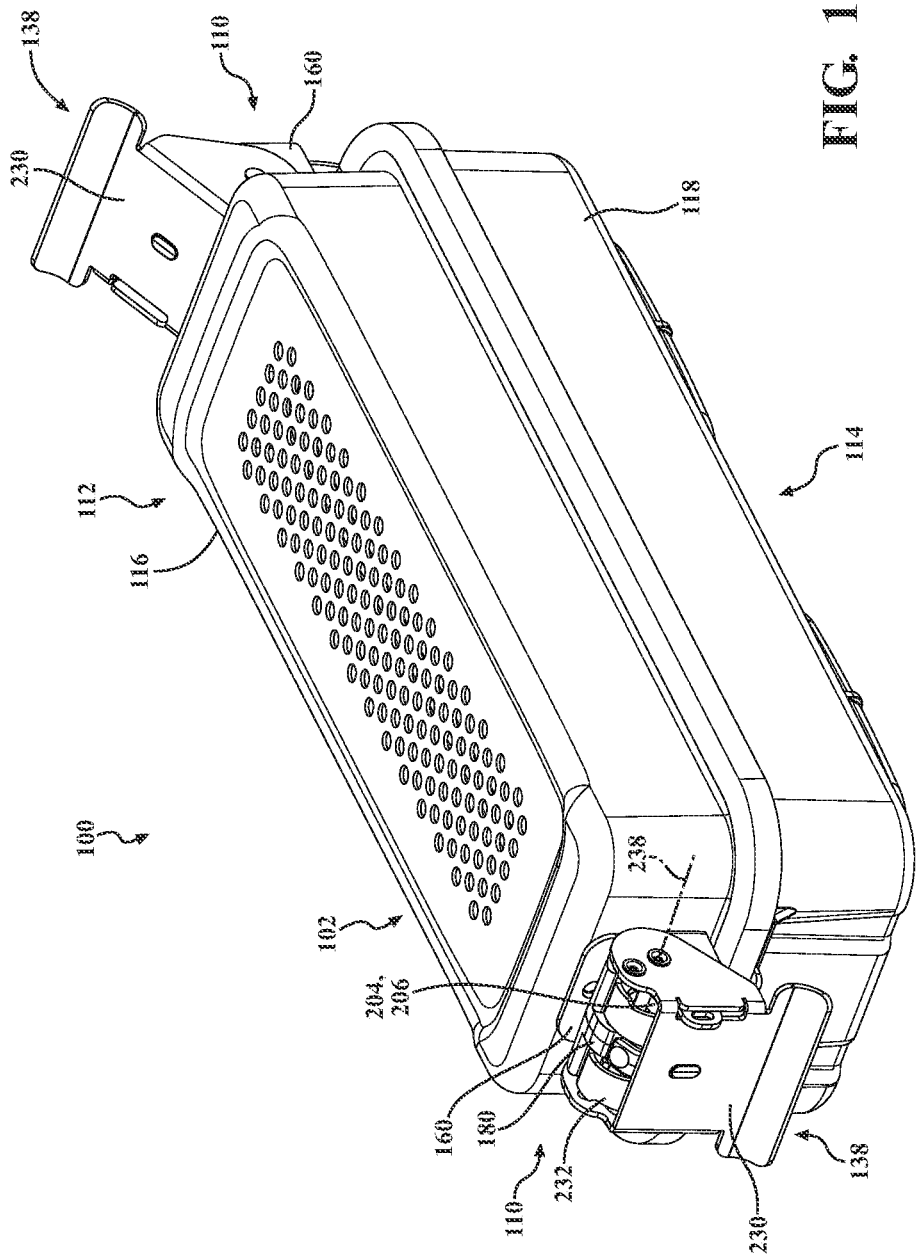
FIG. 1 is a perspective view of sterilization container including a first implementation of a latch.

With reference to the Figures, wherein like numerals indicate like parts throughout the several views, a sterilization container system 100 is shown in FIG. 1. More specifically, FIG. 1 is a perspective view of the sterilization container system 100 that includes a sterilization container 102 for sterilizing surgical and medical instruments and/or tools. In some implementations, the sterilization container system 100 may be utilized to charge a wirelessly chargeable battery. Such an implementation is described more fully in PCT Patent Application No. PCT/US2020/025429, the entire contents of which are incorporated by reference herein. In another alternative instance, the sterilization container 102 may be used to sterilize a surgical instrument other than the wirelessly chargeable batteries. For instance, the methods described herein may be used to sterilize manual surgical instruments, such as scalpels, forceps, and osteo-tomes. The methods described herein may also be used to sterilize powered surgical instruments, such as rotary handpieces, drills, or endoscopes.

In one sterilization method, medical instruments may be placed within the sterilization container 102 prior to sterilization. The sterilization container 102 may then be sterilized in an autoclave process (or other suitable sterilization process) with the medical instruments contained within. Thus, in this method, the medical instruments and the sterilization container 102 may be sterilized together and a volume 120 (shown in FIGS. 4A and 4B) within the sterilization container 102 may be sterilized or maintained in a sterile state. The sterilization container 102 may then be carried or otherwise transported to the desired location of use while maintaining the sterility of the sterile volume 120 and medical instruments.

FIG. 1 illustrates one view of the sterilization container 102. As shown, the sterilization container 102 is substantially rectangular in shape having two sides or ends 110, a top 112, and a bottom 114. However, it should be recognized that the sterilization container 102 may be any suitable shape that enables the sterilization container 102 to operate as described herein.

As shown in FIG. 1, the sterilization container 102 may comprise a lid 116 and a base 118, which are configured for corresponding engagement with one another to collectively define a volume 120 for receiving medical instruments. Better shown in FIGS. 4A-5B, the lid 116 and the base 118 are sealable to one another through use of one or more seals 122 to define the volume 120 within the sterilization container 102. The lid 116 and the base 118 may each include a corresponding outer surface. More specifically, the lid 116 has an outer surface 116A and the base 118 has an outer surface 118A. The lid 116 and the base 118 also include respective inner surfaces 116B, 118B, (shown in FIGS. 4 and 5) which cooperate to define the volume 120. In one instance, the lid 116 is removable from the base 118 to enable one or more medical instruments to be removably placed inside the sterilization container 102.

In some implementations, the lid 116 of the sterilization container 102 may include metal, which may retain heat to facilitate drying of contents thereof. For example, the sterilization container 102 may be placed in an autoclave to sterilize the contents with a high-temperature sterilant, such as steam, hydrogen peroxide, ozone, or ethylene oxide. This may result in liquid condensing on the inside of the sterilization container 102 or the contents disposed therein. After the contents are sterilized and removed from an autoclave, the lid 116 retains heat from the autoclave to facilitate drying of the contents housed within the sterilization container 102. As such, the lid 116 may have a thermal conductivity of greater than or equal to 1 W/(m*K) at 298 Kelvin. In some instances, the lid 116 consists of, or consists essentially of, metal. In other instances, the lid 116 may not include metal. For example, the lid 116 may include a polymeric material. In such instances, the lid 116 may include a material other than metal that still facilitates drying of contents thereof by retaining heat from the autoclave.

The base 118 of the sterilization container 102 includes a material having a glass transition temperature above 140° C. As previously stated, the sterilization container 102 may be placed in an autoclave to sterilize the contents with a high-temperature sterilant. As such, the base 118 includes a material having a glass transition temperature above 140° C. because temperatures inside an autoclave can exceed 120° C. The base 118 of the sterilization container 102 may also include a material permitting the transmission of electromagnetic waves therethrough. As such, the base 118 may include a material having a dielectric constant of less than or equal to ten or a dielectric constant less than or equal to five to permit the transmission of electromagnetic waves therethrough. For example, the base 118 may include a polymeric material permitting the transmission of an electromagnetic wave therethrough, such as a plastic. In another example, the base 118 may include a material other than a polymeric material that permits the transmission of electromagnetic waves therethrough, such as a glass.

In one such instance, the material permitting the transmission of an electromagnetic wave therethrough may be a polymeric material and the base 118 may be formed of the polymeric material via injection molding, thermoforming, machining, 3D printing, and the like. The polymeric material may comprise the poly(aryl ether sulfone) (P) in a weight amount of at least 10%, at least 30% or at least 50%, based on the total weight of the polymeric material. Preferably, the polymeric material comprises the poly(aryl ether sulfone) (P) in a weight amount of at least 70%, based on the total weight of the polymeric material. More preferably, the polymeric material comprises the poly(aryl ether sulfone) (P) in a weight amount of at least 90%, if not at least 95%, based on the total weight of the polymeric material. Still more preferably, the polymeric material consists essentially of the poly(aryl ether sulfone) (P). The most preferably, it consists essentially of the poly(aryl ether sulfone) (P). The poly(aryl ether sulfone) (P) advantageously has a weight average molecular weight in the range of from 20,000 to 100,000. Preferably, the poly(aryl ether sulfone) (P) has a weight average molecular weight in the range of from 40,000 to 70,000. The weight average molecular weight can be determined by Gel Permeation Chromatography using conventional polystyrene calibration standards. The base 118 may comprise a polyphenylsulfone homopolymer, i.e. a polymer of which essentially (and, preferably) all the recurring units are of formula (H). RADEL® R polyphenylsulfone from SOLVAY ADVANCED POLYMERS, L.L.C. is an example of a polyphenylsulfone homopolymer.

Figure 2A:
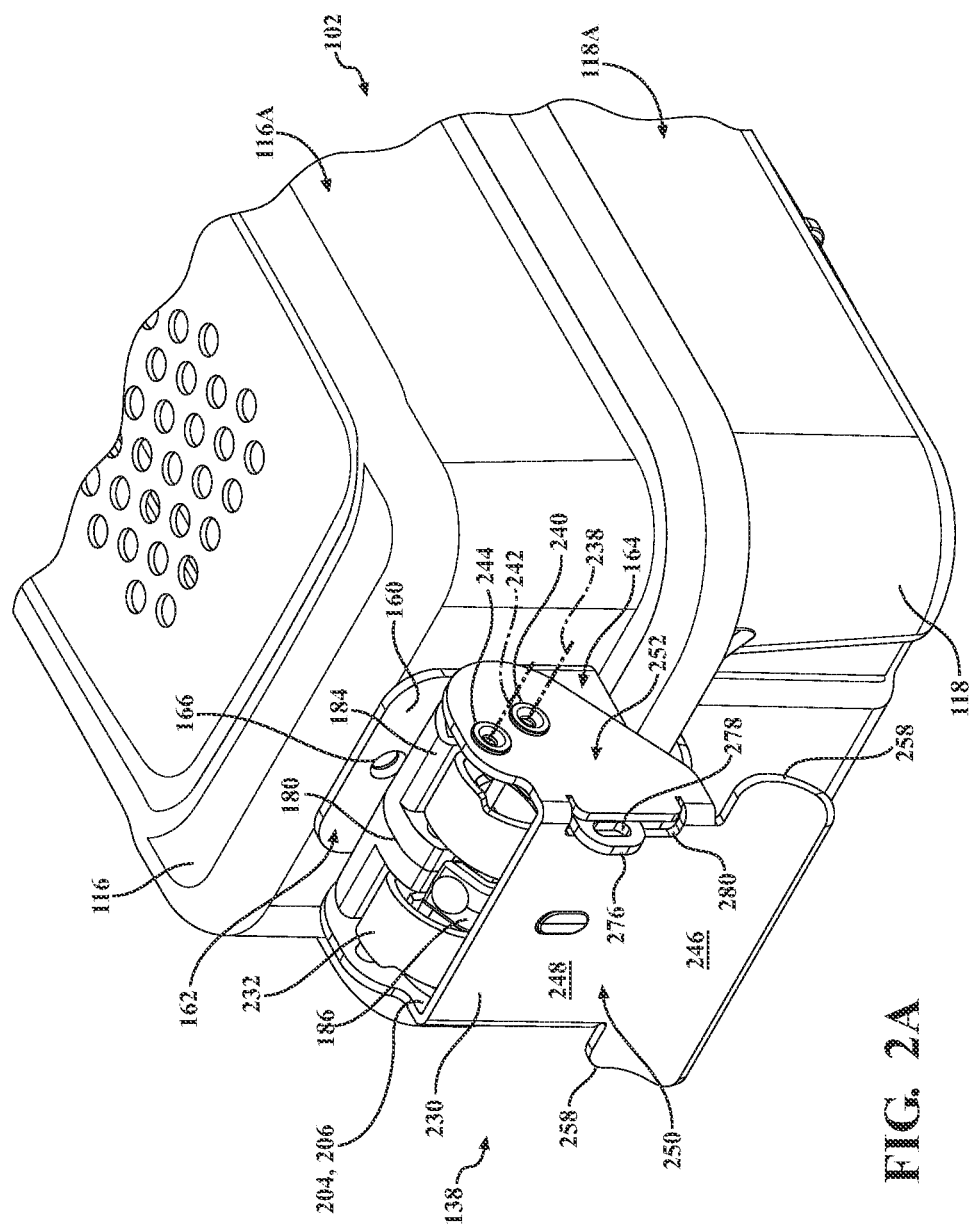
FIG. 2A is a close-up perspective view of the sterilization container and latch of FIG. 1, with the latch shown in a secured position.
Figure 2B:
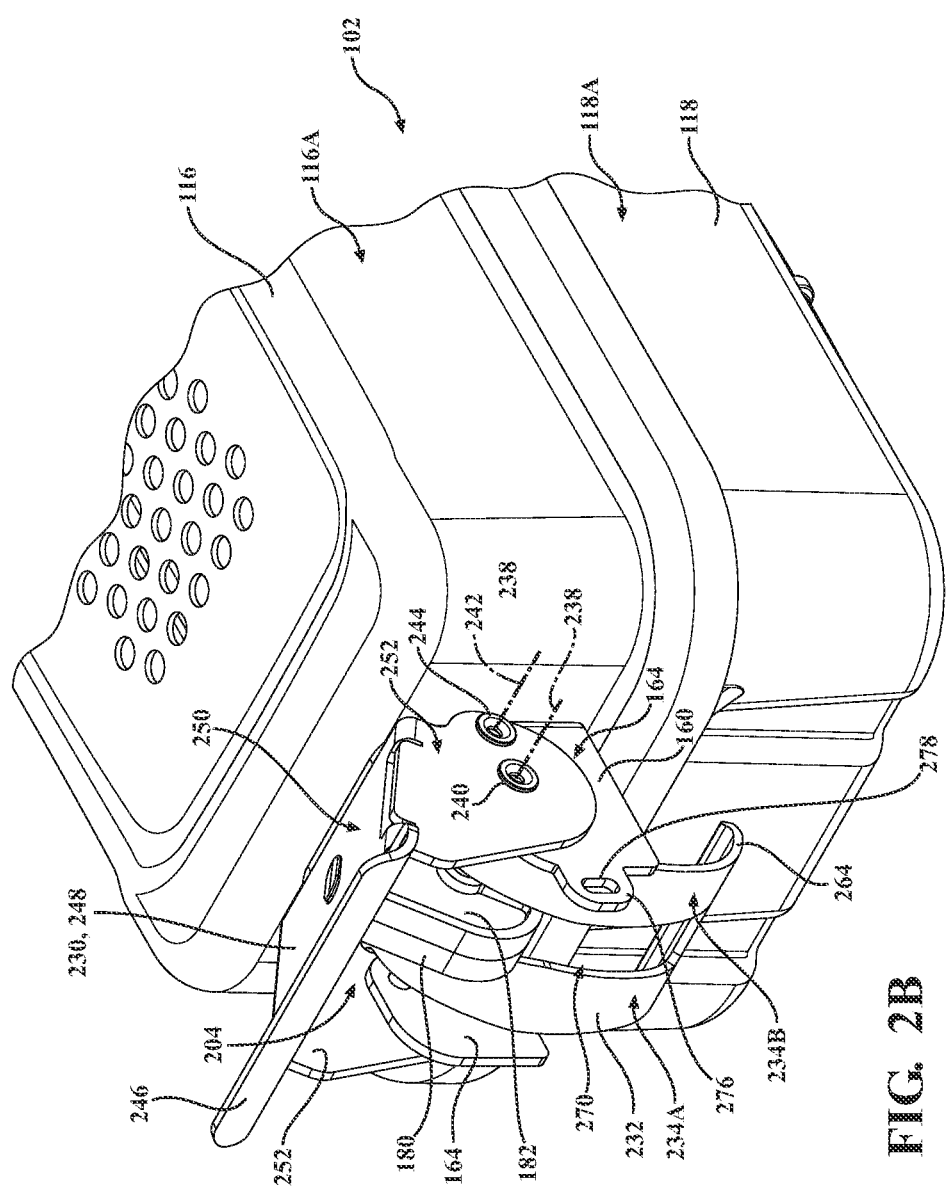
FIG. 2B is a close-up perspective view of the sterilization container and latch of FIG. 1, with the latch shown in an unsecured position.

As shown throughout the figures, and particularly in FIGS. 2A and 2B, the sterilization container 102 may comprise a latch assembly 138. One configuration of the latch assembly 138 is illustrated in FIGS. 2A-9. Another configuration of the latch assembly 138' is shown in FIGS. 12-15 and is discussed in further detail below. Most generally, the latch assembly 138 is attached to one of the lid 116 and the base 118 and allows the user to securely fasten the lid 116 to the base 118 by utilizing mechanical advantage. The sterilization container 102 may comprise more than one latch assembly 138 to facilitate thorough and consistent sealing of the volume 120. In the exemplary sterilization container 102 shown in FIG. 1, two latch assemblies 138 are attached to the lid 116 at opposing ends 110 of the sterilization container 102. In other implementations of the sterilization container (not shown), other quantities of latch assemblies may be used to secure the lid and the base. For example, larger containers may utilize more than one latch assembly per side, or square sterilization containers may utilize one latch on each side, for a total of four latch assemblies.

To this end, the latch assembly 138 may comprise a mount body 160, a lever body 230, and a clasp body 232. As will be described in further detail below, the mount body 160 may be fixedly coupled to the lid 116, the lever body 230 may be coupled to the mount body 160, and the clasp body 232 may be coupled to the lever body 230. In some configurations the mount body 160 may be coupled to the base 118 and configured such that the clasp body 232 engages the lid 116 to fasten the base 118 to the lid 116. The lever body 230 is pivotably coupled to the mount body 160 such that the lever body 230 is moveable between an unsecured position and a secured position. By moving the lever body 230 between the secured position and unsecured position, a user may secure/unsecure the lid 116 to/from the base 118 without needing to separately touch the clasp body 232 (described below). As illustrated herein, figures designated with "A" correspond to the secured position, and figures designated with "B" correspond to the unsecured position (with the exception of FIG. 3B). Specifically, in FIGS. 2A, 3A, 4A, and 5A, the latch assembly 138 is shown in the secured position, and in FIGS. 2B, 3C, 4B, and 5B the latch assembly 138 is shown in the unsecured position. As will be discussed below, in FIG. 3B the latch assembly 138 is shown in an intermediate position between the secured position and the unsecured position.

Shown best in FIGS. 5A and 5B, the base 118 may comprise a lip 148 integrally formed with the base 118. This is advantageous because, during transfer of the sterilization container 102, the base 118 may contact a non-sterile surface. More generally stated, when removing sterile contents from the sterilization container 102, it is advantageous to limit contact between a user and the sterilization container 102 when removing the sterile contents. As such, because the user may remove the lid 116 of the sterilization container 102 from the base 118 of the sterilization container 102 without separately contacting the base 118 and/or the clasp body 232, the user is able to remove sterile contents from the sterilization container 102 in a sterile manner.

As mentioned above, the mount body 160 may be fixedly coupled to the lid 116, and as shown in the figures, may be connected to one of the ends 110 of the lid 116. Here, the lid 116 includes two latch assemblies 138, which are arranged on the shorter of two pairs of opposing sides. Best shown in FIGS. 4A and 4B, the mount body 160 comprises a back portion 162 coupled to the lid 116 and two side portions 164 that extend from the back portion 162 away from the lid 116. Better shown in FIG. 7, several features may be defined in the two side portions 164, a pivot bore 236 is defined in the mount body 160 and extends between each of the side portions 164 and defines a pivot axis 238. The pivot axis 238 is generally parallel to the side of the lid 116 and configured to receive a pivot shaft 240, as will be discussed in further detail below. The back portion 162 of the mount body 160 may define a mount body recess 166 sized and shaped to receive a tab 186 for holding the lever body 230 in the unsecured position. The mount body recess 166 shown here is in the form of a circular depression formed in the back portion 162 and facing the lever body 230.

Figure 7:
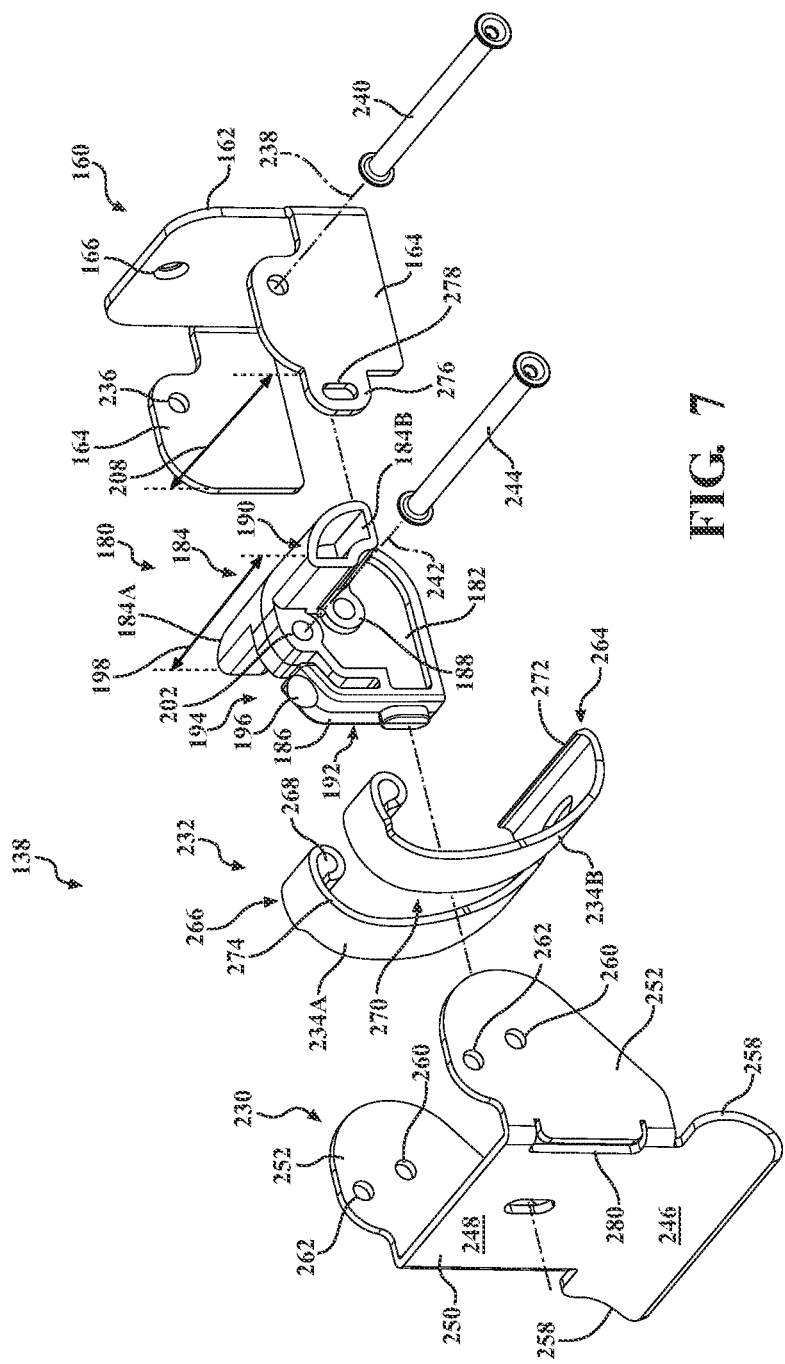
FIG. 7 is an exploded view of the latch of FIG. 6 including a deflector.

Operation of the latch assembly 138 is effected via the lever body 230. The lever body 230 has a handle portion 246 and a body portion 248, the handle portion 246 is configured to be grasped by a user in furtherance of operating the latch assembly 138 and the body portion 248 is configured to effect coordinated movement of the latch assembly 138 in response to actuation of the handle portion 246. The body portion 248 of the lever body 230 may comprise a front wall 250 and two side walls 252. The side walls 252 extend in a generally perpendicular direction from opposing sides of the front wall 250 toward an edge. The front wall 250 and the side walls 252 may be formed, for example, by bending opposite edges of a flat material to form a U shape. A pair of wings 258 protrude from the front wall 250 in a generally parallel direction to partially form the handle portion 246 of the lever body 230. As shown in FIG. 7, a pivot aperture 260 and a link aperture 262 are defined in the body portion 248 of the lever body 230, each extending through at least one of the side walls 252. The pivot aperture 260 is configured to receive the pivot shaft 240 and the link aperture 262 is configured to receive a link shaft 244, also discussed in further detail below. The link aperture 262 is radially spaced from the pivot axis 238 such that, when viewed from a direction parallel with the pivot axis 238, the link aperture 262 traces an arcuate path as the lever body 230 is moved between the secured position and the unsecured position.

The lever body 230 is disposed on the mount body 160 with the side walls 252 positioned adjacent to the side portions 164 of the mount body 160 such that the pivot aperture 260 in the side walls 252 are aligned with the pivot bore 236 of the mount body 160. The pivot shaft 240 is inserted through the pivot apertures 260, thereby pivotably coupling the lever body 230 to the mount body 160. The mount body 160 and the lever body 230 cooperate to define a latch interior 204 when coupled, and further define an opening 206 of the latch interior 204 when the lever body 230 is in the secured position. The interior 204 defines an interior width 208 (FIG. 7), which may be measured between each of the side portions 164 of the mount body 160.

Turning now to FIGS. 3A-3C, the lever body 230 is shown in a secured position (FIG. 3A), an intermediate position (FIG. 3B), and an unsecured position (FIG. 3C). The lever body 230 is pivotable, relative to the mount body 160, about the pivot axis 238 between the secured position and the unsecured position. The secured position is generally defined by the lever body 230 being arranged approximately parallel to the back portion 162 of the mount body 160, and the handle portion 246 positioned relatively near the base 118 of the sterilization container 102. The unsecured position is generally defined by the lever body 230 being arranged approximately perpendicular to the back portion 162 of the mount body 160, and the handle portion 246 positioned relatively far from the base 118 of the sterilization container 102. Said differently, the handle portion 246 is positioned closer to the base 118 in the secured position than in the unsecured position. While parallel and perpendicular are used to generally describe the position the lever body 230 with respect to other features of the latch assembly 138, they are merely terms of description rather than precise measurements of the position of the specific components to which they are referencing. In this way, it is contemplated that in the secured position the front wall 250 of the lever body 230 could be at an angle that is within approximately 30° of parallel to the back portion 162 of the mount body 160. Likewise, in the unsecured position the front wall 250 of the lever body 230 could be at an angle that is within approximately 30° of perpendicular to the back portion 162 of the mount body 160.

In addition to being disposed in both the pivot bore 236 and the pivot aperture 260, the pivot shaft 240 may be secured in position or to either of the lever body 230 and/or the mount body 160 via several methods. For example, one exemplary method may enlarge opposing ends of the pivot shaft 240 to prevent the pivot shaft 240 from sliding out of the pivot apertures 260. Alternatively, a press fit between the pivot shaft 240 and the pivot bore 236 such that the lever body 230 pivots relative to the pivot shaft 240 may be utilized. A press fit between the pivot shaft 240 and the pivot aperture 260 may be utilized such that the pivot shaft 240 moves with the lever body 230 relative to the mount body 160 may also be utilized. Further methods, such as staking, fasteners, welding, and the like may also be utilized either in the alternative or in combination.

Turning to FIGS. 6 and 7, movement of the lever body 230 is transferred to the base 118 via the clasp body 232, which is coupled to the lever body 230. The clasp body 232 has an interface end 264 and a link end 266. The interface end 264 is configured to engage the lip 148 of the base 118 for tensioning the lid 116 toward the base 118. The link end 266 defines a clasp bore 268 and a link axis 242, which is configured to receive the link shaft 244 such that the clasp body 232 is coupled to the lever body 230 and movable about the link shaft 244. Movement of the link end 266 of the clasp body 232 corresponds to movement of the link aperture 262 in the lever body 230, which moves about a semi-circular arc about the pivot axis 238 as the lever body 230 moves between the secured position and the unsecured position. As shown in FIGS. 6 and 7, the clasp body 232 may further comprise two clasp portions 234A, 234B with a pocket 270 defined therebetween. Said differently, the clasp body 232 comprises a first clasp portion 234A and a second clasp portion 234B with a pocket 270 defined therebetween. The clasp portions 234A, 234B extend between the interface end 264 and the link end 266 and are spaced so as to receive a portion of the lever body 230 in the pocket 270 as the lever body 230 is moved toward the secured position.

In some configurations, the clasp bore 268 may be formed on the link end 266 of the clasp body 232 by bending an end of each of the clasp portions 234A, 234B around and back toward the interface end 264 at a radius suitable to receive the link shaft 244. The interface end 264 may be similarly bent to form a hooked profile 272 that is suitable to engage the lip 148 of the base 118 such that when the clasp body 232 is engaging the base 118 and the lever body 230 is in the secured position the interface end 264 is not readily disengaged. In other instances, such as instances wherein the interface end 264 does not include the hooked profile 272 and/or the base 118 does not include the lip 148, the interface end 264 may be configured to engage with the base 118 via alternative means.

In addition to the hooked profile 272, the clasp body 232 may be formed with an arcuate profile 274 between the interface end 264 and the link end 266. Said differently, the first and second clasp portions 234A, 234B may be curved between the interface end 264 and the link end 266. A clasp offset R3 is defined between the clasp body 232 and the pivot axis 238. The clasp offset R3 is a measurement of the distance between an outer surface of the clasp body 232 and the pivot axis 238.

With renewed reference to FIGS. 1-2B, in some instances, a frangible sealing element (not shown) may be coupled to the latch assembly 138. The frangible sealing element may be configured to indicate whether the latch assembly 138 is in the unsecured position or the secured position. Here, the mount body 160 may include a flange extending away from the lid 116. The flange may have a lock portion 276 that defines a security aperture 278. The lever body 230 may further define a shear aperture 280 arranged on the body portion 248 and extending through the front wall 250. The shear aperture 280 is arranged such that as the lever body 230 is moved toward the secured position the shear aperture 280 receives the lock portion 276 of the flange and in the unsecured position the shear aperture 280 is spaced from the lock portion 276. By moving the lever body 230 from the secured position to the unsecured position, the shear aperture 280 of the lever body 230 severs the frangible sealing element. Furthermore, the frangible sealing element may be disposed in the security aperture 278 of the mount body 160. As such, when the lever body 230 is moved to the secured position and the frangible sealing element is disposed in the security aperture 278, the frangible sealing element will be severed by the shear aperture 280 when the lever body 230 is moved to the unsecured position.

In various instances, the latch assembly 138 may vary. Additionally, as previously stated, while the base 118 includes a lip 148 and the interface end 264 of the clasp body 232 includes a hooked profile 272, in other instances the interface end 264 may not include the hooked profile 272 and/or the base 118 may not include the lip 148. In such instances, the interface end 264 may be configured to engage with the base 118 via alternative means.

As mentioned above, the link shaft 244 is disposed in the link aperture 262 and the clasp bore 268. Similar to the pivot shaft 240 described above, the link shaft 244 may be secured to the link aperture 262 or the clasp bore 268 by various methods such as, for example, a press fit, welding, fasteners, adhesives, enlarging the ends, and the like. For example, one exemplary method may enlarge each end of the link shaft 244 using a press, which prevents the link shaft 244 from being removed. Alternatively, a press fit between the link shaft 244 and the clasp bore 268 such that the lever body 230 moves freely on the link shaft 244 may be utilized. A press fit between the link shaft 244 and the link aperture 262 may be utilized such that the clasp body 232 moves freely on the link shaft 244 may also be utilized.

Returning to FIGS. 4A-9, the latch assembly 138 may further comprise a deflector 180 positioned at least partially within the interior 204 defined by the mount body 160 and the lever body 230. The deflector 180 is movable with the lever body 230 for concurrent movement about the pivot axis 238. As the lever body 230 is pivoted between the secured position and the unsecured position, the deflector 180 pivots about the pivot axis 238 in a similar manner. The deflector 180 may comprise a hub portion 182, a wing portion 184, and a tab 186. The hub portion 182 is supported on the pivot axis 238 and defines a hub bore 188. The hub bore 188 is sized and shaped to receive the pivot shaft 240 and aligned with the pivot axis 238. The hub portion further defines a link bore 202 radially spaced from the hub bore 188. The link bore 202 is aligned with the link axis 242 and sized and shaped to receive the link shaft 244. As will be discussed in further detail below, the link bore 202 is positioned at a third angular location 214. The hub portion 182 has a width that is sized to fit within the pocket 270 between the clasp portions 234A, 234B of the clasp body 232, and as such, the clasp body 232 moves around the deflector 180 as the lever body 230 is moved between the secured position and the unsecured position. The Best shown in FIGS. 7-9, the deflector 180 may comprise the wing portion 184, which may extend from the hub portion 182 and define an outer surface 190 spaced from the pivot axis 238. The outer surface 190 is positioned adjacent to the opening 206 of the latch interior 204 when the lever body 230 is in the secured position. The wing portion 184 is arranged such that the outer surface 190 prevents access to the latch interior 204 through the opening 206. As will be appreciated by FIGS. 3A-3C, the opening 206 opens toward the top 112 of the sterilization container 102, and as the lever body 230 is moved from the secured position (FIG. 3A), through the intermediate position (FIG. 3B), and toward the unsecured position (FIG. 3C), the size of the opening 206 decreases. Due to the location of the opening 206 relative to the lid 116, the opening 206 presents a potential pinch point for the user during use. More specifically, while opening the sterilization container 102 a user may position one of their fingers in or near the opening 206, and as lever body 230 is pivoted toward the unsecured position the user's finger(s) may be pinched between the lever body 230 and the lid 116.

In order to minimize the possibility of the user being pinched by the lever body 230, the wing portion 184 of the deflector 180 shields the opening 206 of the latch interior 204, preventing the user's fingers from passing through the opening 206. In order to block the opening 206, the wing portion 184 extends from the hub portion 182 in a direction substantially parallel to the pivot axis 238 and defines a deflector width 198. The wing portion 184 is positioned on the hub portion 182 at a first angular location 210 relative to the pivot axis 238. Said differently, the wing portion 184 is radially spaced from the pivot axis 238 and defines the first angular location 210. In FIG. 5B, the first angular location 210 is illustrated at an upper right position relative to the hub bore 188. In FIG. 5A, the first angular location 210 is illustrated at a bottom position relative to the hub bore 188.

In order to further minimize the possibility of a user being pinched, the wing portion 184 extends from the hub portion 182 such that the opening 206 is blocked so as to prevent a user's fingers, and other objects, from being pinched by the latch assembly 138. As such, the wing portion 184 may be sized and shaped so as to reduce the open area of the opening 206. The opening 206 may be reduced such that the measurement of any remaining open area is smaller than a user's finger, substantially eliminating the risk of being pinched. Because it is not necessary to completely block the opening 206, the wing portion 184 need not extend the entire distance of the interior width 208. Sufficiently shielding the opening 206 may be accomplished with a deflector width 198 that is 65% of the interior width 208. Said differently, a ratio of the deflector width 198 to the interior width 208 may be 0.65. In other implementations the ratio of the deflector width 198 to the interior width 208 may be greater than 0.65, such as 0.75, 0.85, or 0.95.

Figure 9:
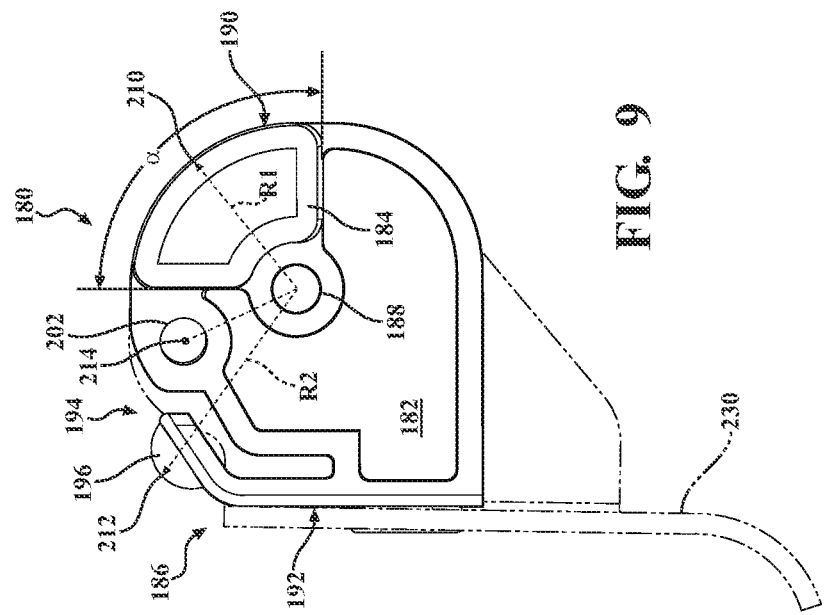
FIG. 9 is a side view of the deflector of FIG. 8.
Figure 8:
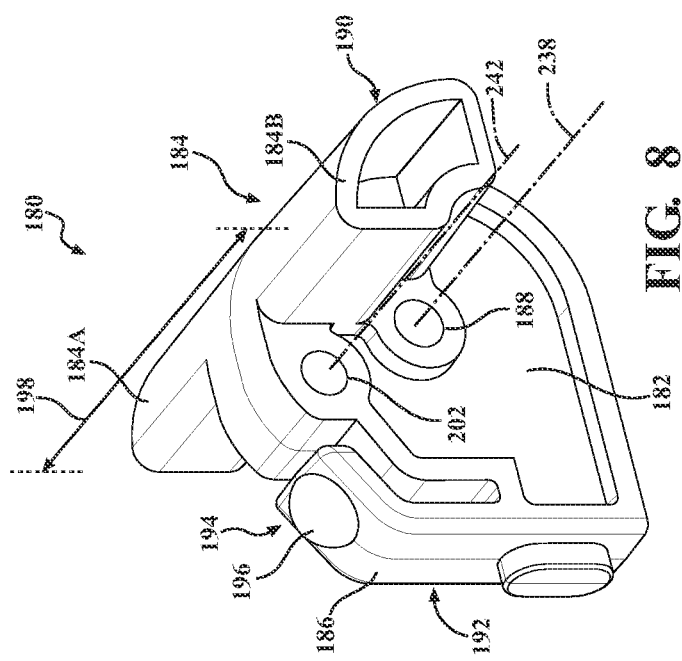
FIG. 8 is a perspective view of the deflector of FIG. 7
Figure 10:
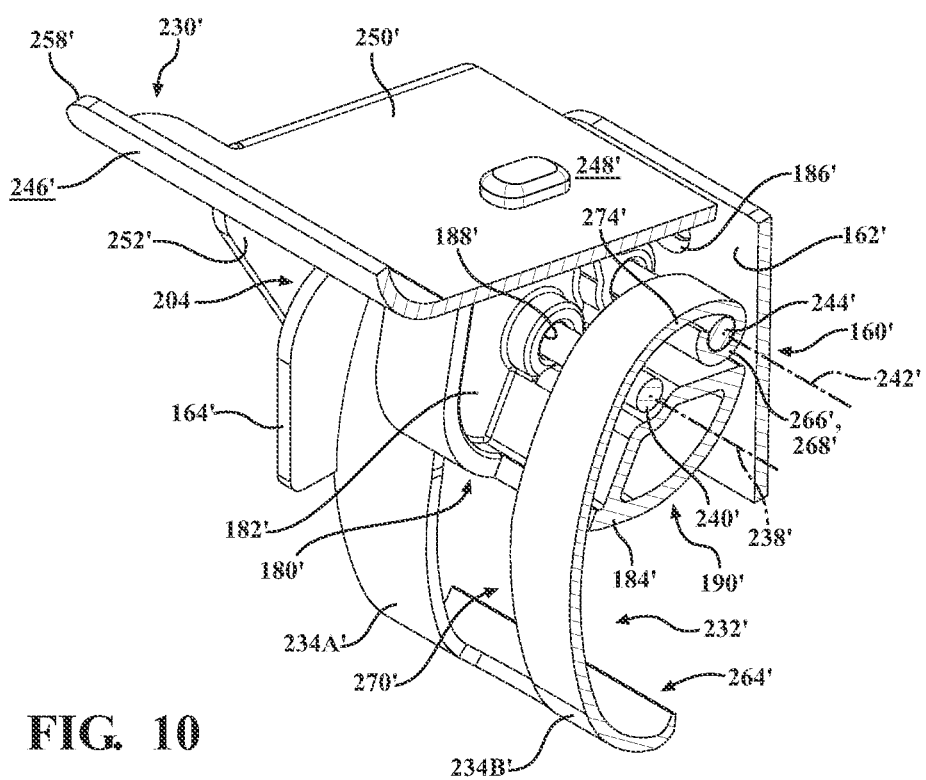
FIG. 10 is a cross-sectional perspective view of a second implementation of the latch.
Figure 11:
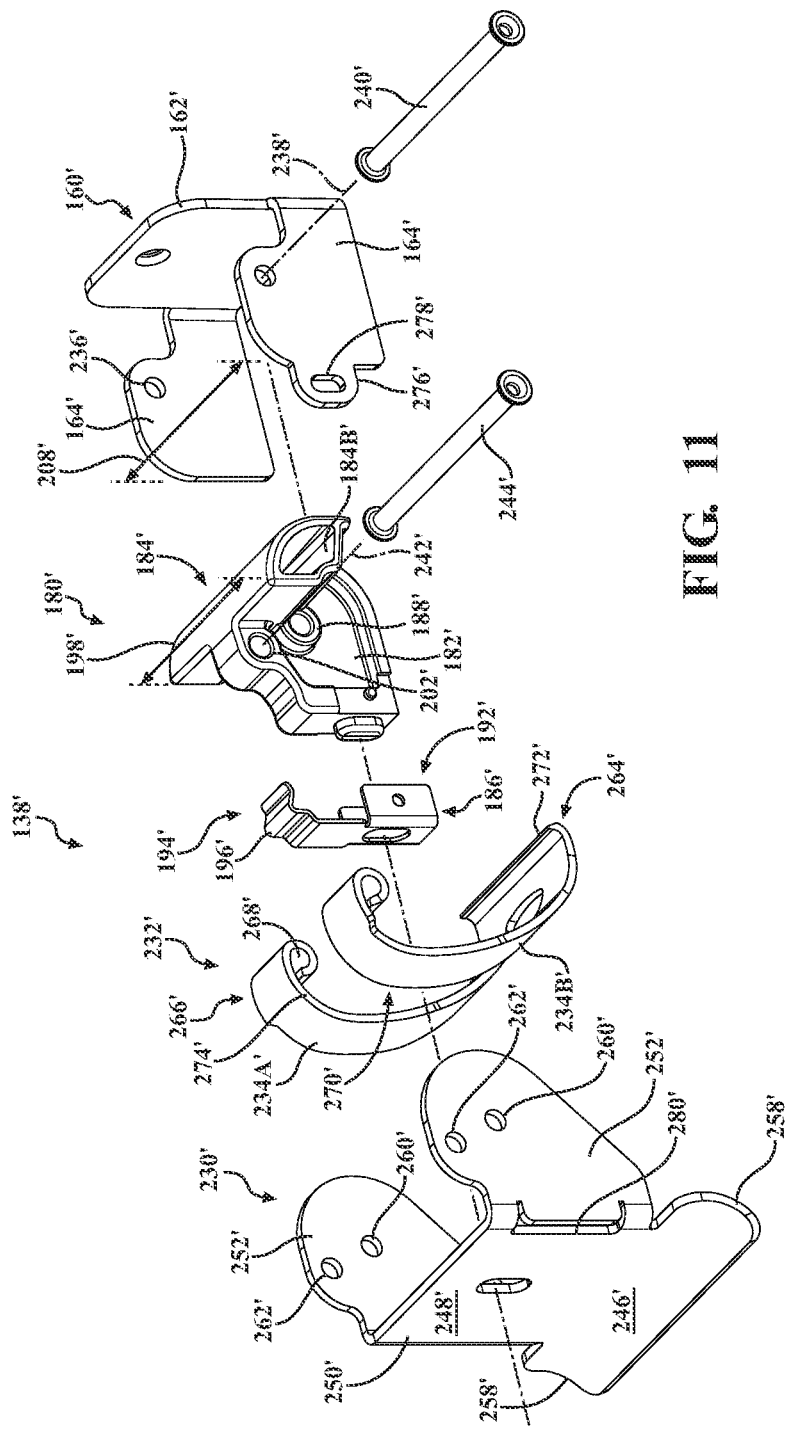
FIG. 11 is an exploded view of the latch of FIG. 10 including a deflector.
Figure 13:
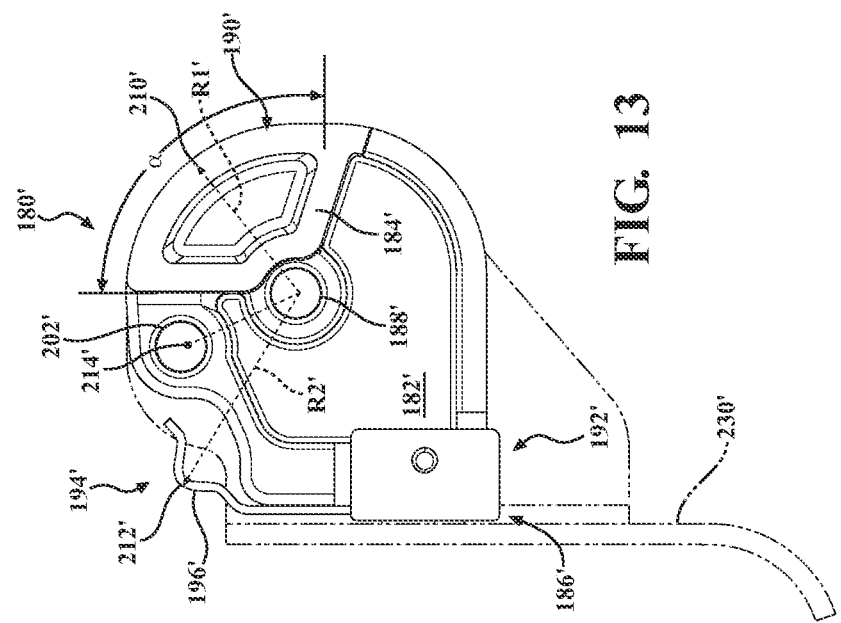
FIG. 13 is a side view of the deflector of FIG. 12.
Figure 12:
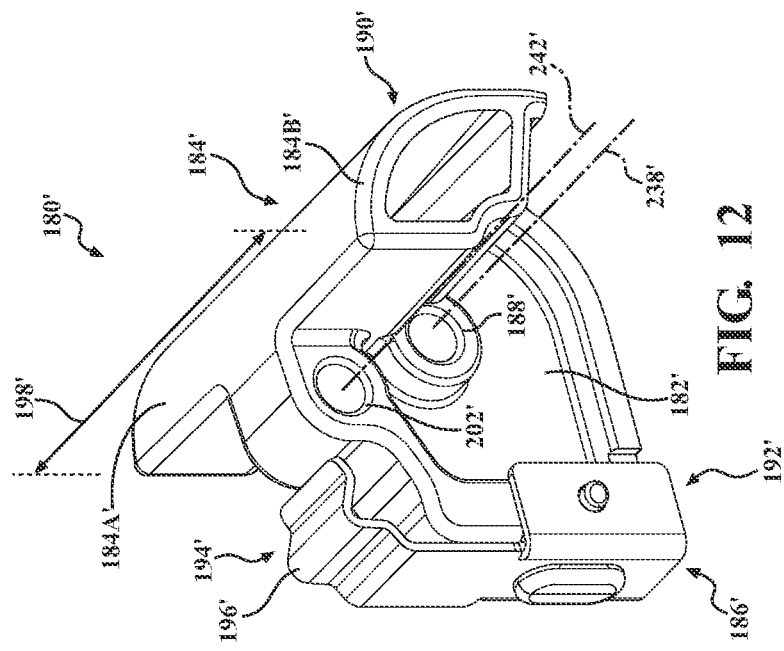
FIG. 12 is a perspective view of the deflector of FIG. 11

In addition to the deflector width 198, the wing portion 184 further defines an arc angle α, shown in FIG. 9. The arc angle is an angular measurement of the outer surface 190 of the wing portion 184. Here, the arc angle α defined by the wing portion 184 may be greater than 75°. In the implementation illustrated herein, the arc angle α may be greater than 90°. The arc angle α may be measured from the first angular location 210. Said differently, the arc angle α may be centered at the first angular location 210. The deflector 180 further defines a first deflector radius R1 between the pivot axis 238 and the first angular location 210. The first deflector radius R1 is the distance from an outermost point of the wing portion 184 at the first angular location 210 and the pivot axis 238. When the lever body 230 is in the secured position the first deflector radius R1 is approximately equal to the clasp offset R3.

In the implementation of the deflector 180 shown here, the wing portion 184 may comprise a first wing portion 184A and a second wing portion 184B, each extending from the hub portion 182. The first wing portion 184A may extend in a first axial direction and the second wing portion 184B may extend in a second axial direction. Here, the first axial direction and the second axial direction are opposite to each other and parallel to the pivot axis 238. As shown here, the hub portion 182 is generally positioned in the middle of the interior 204 between the side portions 164 of the mount body 160, and as such, each of the first wing portion 184A and the second wing portion 184B extends approximately from the hub portion 182, toward the corresponding side portion, approximately the same distance.

In addition to the wing portion 184, the deflector 180 comprises the tab 186. The tab 186 is coupled to the hub portion 182 separate from the wing portion 184. The tab 186 may engage the mount body 160 when the lever body 230 is in the unsecured position for retaining the lever body 230 in the unsecured position. The tab 186 may alternatively engage the lid 116 when the lever body 230 is in the unsecured position for retaining the lever body 230 in the unsecured position. Similarly, the tab 186 may be disengaged from the mount body 160 when the lever body 230 is in the secured position. As such, the tab 186 may limit free movement of the lever body 230 from the unsecured position to the secured position.

As mentioned above, the tab 186 limits free movement of the lever body 230, which is effected via engagement between the tab 186 and the lever body 230. To this end, the tab 186 extends between a fixed end 192 coupled to the hub portion 182 and a free end 194 spaced from the hub portion 182. The free end 194 of the tab 186 may comprise a protrusion 196, which defines a second angular location 212 (discussed below). The second angular location 212 being spaced from the first angular location 210. The tab 186 may be formed such that the free end 194 is spaced from the hub portion 182. When the tab 186 is formed from a flexible material, space between the free end 194 and the hub portion 182 allows the free end 194 to move relative closer to the hub portion 182. Turning to FIG. 7, the protrusion 196 is able to engage the mount body recess 166 of the mount body 160 to hold the lever body 230 in the unsecured position. Moving the lever body 230 into, or out of, the unsecured position flexes the tab 186, adding resistance to the movement.

Shown best in FIGS. 5A and 9, the deflector 180 further defines a second deflector radius R2 between the pivot axis and the protrusion 196. The second deflector radius R2 is the distance from an outermost point of the protrusion 196 at the second angular location 212 and the pivot axis 238. The second deflector radius R2 is greater than the first deflector radius R1. The increased distance to the protrusion 196 means that the free end 194 of the tab 186 must be flexed toward the hub portion 182 when the lever body 230 is moved into or out of the unsecured position. Additionally, the second deflector radius R2 is greater than the clasp radius R3. Said differently, the clasp offset R3 is less than the second deflector radius R2.

Pivoting movement of the lever body 230 can be defined relative to the angular locations on the deflector 180. The first angular location 210 is spaced from the second angular location 212 with the third angular location 214 positioned therebetween. As illustrated herein, an angular measurement between the first angular location 210 and the second angular location 212 may be less than 90°. When the lever body 230 is in the secured position, the first angular location 210 is nearer to the base 118 and the lid 116 of the sterilization container 102 than the second angular location 212. When the lever body 230 is in the unsecured position, the second angular location 212 is nearer to the base 118 and the lid 116 of the sterilization container 102 than the first angular location 210.

Referring again to the side views shown in FIGS. 3A-3C, where the latch assembly 138 is shown in the secured position, the intermediate position, and the unsecured position along with corresponding movement of the clasp body 232. Movement of the lever body 230 toward the unsecured position moves the clasp body 232 to disengage the interface end 264 from the lip 148 of the base 118. As the lever body 230 is pivoted the link shaft 244 moves in a semi-circular arc, such that the link shaft 244 moves from a position generally above the pivot shaft 240 to a position generally below the pivot shaft 240 and the link end 266 of the clasp body 232 moves in a downward direction.

Furthermore, movement of the clasp body 232 can be partly defined by the position of the wing portion 184 of the deflector 180. The wing portion 184 of the deflector 180 is spaced from the clasp body 232 when the lever body 230 is in the secured position and as the lever body 230 and the deflector 180 pivot about the pivot axis 238 away from the secured position, the wing portion 184 engages the clasp body 232 such that as the lever body 230 is further pivoted toward the unsecured position the wing portion 184 moves the interface end 264 away from the base 118. In some implementations, the intermediate position of the lever body 230 may be defined at a position where the wing portion 184 contacts the clasp body 232. At this intermediate position the wing portion 184 engages one of the clasp portions 234A, 234B of the clasp body 232 and as the lever body 230 is further pivoted toward the unsecured position the clasp body 232 pivots around the pivot axis 238 and the interface end 264 moves away from the base 118. Alternatively, in the intermediate position movement of the lever body 230 toward the secured position causes the wing portion 184 to become spaced from the clasp body 232 such that the hooked profile 272 can engage the lip 148 of the base 118. Similarly, the pivot shaft 240 may protrude from the hub portion 182 such that the pivot shaft 240 is spaced from the clasp body 232 when the lever body 230 is in the secured position. As the lever body 230 is pivoted away from the secured position, the pivot shaft 240 may engage the clasp body 232 such that further pivoting of the lever body 230 toward the unsecured position moved the interface end 264 of the clasp body 232 away from the base 118 and lip 148.

Attaching and detaching the lid 116 from the base 118 is advantageously performed simultaneously with actuation of the latch assembly 138 because motion of the lever body 230 shares a component direction with the direction that the lid 116 moves relative to the base 118 during attaching and detaching. Owing to the configuration of the latch assembly 138, movement of the handle portion 246 to engage the lid 116 with the base 118 is continuous with pivoting of the lever body 230 from the unsecured position to the secured position, therefore the lid 116 can be coupled to the base 118 with a single motion. Specifically, with the lever body 230 in the unsecured position a user grasps the handle portion 246 and moves the lid 116 downward to engage the base 118, upon engagement of the lid and the base 118 the user continues with the downward motion to pivot the lever body 230 from the unsecured position to the secured position, thereby moving the clasp body 232 into engagement with the base 118 and securing the lid 116 to the base 118.

The latch assembly 138 is configured to effect disengaging the lid 116 from the base 118 in a similarly continuous movement. Pivoting the lever body 230 toward the unsecured position to effect disengagement of the interface end 264 of the clasp body 232 from the lip 148 of the base 118 is continuous with movement of the handle portion 246 to disengage the lid 116 from the base 118. Specifically, with the lever body 230 in the secured position as shown in FIG. 3A, a user grasps the handle portion 246 and pivots the lever body 230 toward the unsecured position by way of the intermediate position shown in FIG. 3B, causing the interface end 264 of the clasp body 232 to move downward and disengage from the lip 148. In the intermediate position, the link end 266 of the clasp body 232 has moved downward such that one of the clasp portions 234A, 234B contacts the wing portion 184. As the user continues to move the lever body 230 toward the unsecured position the handle portion 246 moves upwardly, which causes the link end 266 to correspondingly move downward. Due to the contact between the clasp body 232 and the wing portion 184, the interface end 264 moves outwardly away from the lip 148, and upon reaching the unsecured position as shown in FIG. 3C the user continues with the upward movement to lift the lid 116 away from the base 118. Due to the contact between the clasp body 232 and the pivot shaft 240 which causes coordinated movement between the lever body 230 and the clasp body 232, the user is not required to perform a secondary step of disengaging the interface end 264, and as such can remove and attach the lid 116 to the base 118 by only contacting the handle portion 246 of the lever body 230.

Turning now to FIGS. 10-13, another version of a latch assembly and deflector are shown. As will be appreciated from the subsequent description below, the second latch assembly and deflector are similar to the latch assembly 138 and deflector 180 described above in connection with FIGS. 2A-9. As such, the components and structural features of the second version of the latch assembly 138' and deflector 180' that are the same as, or that otherwise correspond to, the first version of the latch assembly 138 and deflector 180 are provided with the same reference numerals with the addition of a prime symbol (e.g., 138 and 138'). While the specific differences between these versions will be described in detail, for the purposes of clarity, consistency, and brevity, only certain structural features and components common between these versions will be discussed and depicted in the drawings of the second version of the latch assembly 138' and deflector 180'. Here, unless otherwise indicated, the above description of the first version of the latch assembly 138 and deflector 180 may be incorporated by reference with respect to the second version of the latch assembly 138' and deflector 180' without limitation.

Similar to above, the latch assembly 138' may comprise a mount body 160', a lever body 230', and a clasp body 232'. As will be described in further detail below, the mount body 160' may be fixedly coupled to the lid, the lever body 230' may be coupled to the mount body 160', and the clasp body 232' may be coupled to the lever body 230'. In some configurations the mount body 160' may be coupled to the base and configured such that the clasp body 232' engages the lid to fasten the base to the lid. The lever body 230' is pivotably coupled to the mount body 160' such that the lever body 230' is moveable between an unsecured position and a secured position. By moving the lever body 230' between the secured position and unsecured position, a user may secure/unsecure the lid to/from the base without needing to separately touch the clasp body 232'.

Here too, the mount body 160' comprises a back portion 162' coupled to the lid and two side portions 164' that extend from the back portion 162' away from the lid. Several features may be defined in the two side portions 164', a pivot bore 236' is defined in the mount body 160' and extends between each of the side portions 164' and defines a pivot axis 238'. The pivot axis 238' is generally parallel to the side of the lid and configured to receive a pivot shaft 240'. The back portion 162' of the mount body 160' may define a mount body recess 166' sized and shaped to receive a tab 186' for holding the lever body 230' in the unsecured position. The mount body recess 166' shown here is in the form of a circular depression formed in the back portion 162' and facing the interior 204'.

The lever body 230' has a handle portion 246' and a body portion 248', the handle portion 246' is configured to be grasped by a user in furtherance of operating the latch assembly 138' and the body portion 248' is configured to effect coordinated movement of the latch assembly 138' in response to actuation of the handle portion 246'. The body portion 248' of the lever body 230' may comprise a front wall 250' and two side walls 252'. The side walls 252' extend in a generally perpendicular direction from opposing sides of the front wall 250' toward an edge. The front wall 250' and the side walls 252' may be formed, for example, by bending opposite edges of a flat material to form a U shape. A pair of wings 258' protrude from the front wall 250' in a generally parallel direction to partially form the handle portion 246' of the lever body 230'. A pivot aperture 260' and a link aperture 262' are defined in the body portion 248' of the lever body 230', each extending through at least one of the side walls 252'. The pivot aperture 260' is configured to receive the pivot shaft 240' and the link aperture 262' is configured to receive a link shaft 244'. The link aperture 262' is radially spaced from the pivot axis 238' such that, when viewed from a direction parallel with the pivot axis 238', the link aperture 262' traces an arcuate path as the lever body 230' is moved between the secured position and the unsecured position.

The lever body 230' is disposed on the mount body 160' with the side walls 252' positioned adjacent to the side portions 164' of the mount body 160' such that the side aperture 260' in the side walls 252' are aligned with the pivot bore 236' of the mount body 160'. The pivot shaft 240' is inserted through the pivot apertures 260', thereby pivotably coupling the lever body 230' to the mount body 160'. The mount body 160' and the lever body 230' cooperate to define a latch interior 204' when coupled, and further define an opening 206' of the latch interior 204' when the lever body 230' is in the secured position.

The latch assembly 138' may further comprise a deflector 180' positioned at least partially within the interior 204' defined by the mount body 160' and the lever body 230'. The deflector 180' is movable with the lever body 230' for concurrent movement about the pivot axis 238'. As the lever body 230' is pivoted between the secured position and the unsecured position, the deflector 180' pivots about the pivot axis 238' in a similar manner. The deflector 180' may comprise a hub portion 182', a wing portion 184', and a tab 186'. The hub portion 182 is supported on the pivot axis 238' and defines a hub bore 188' sized and shaped to receive the pivot shaft 240'. The hub portion 182' has a width that is sized to fit within the pocket 270' between the clasp portions 234A', 234B' of the clasp body 232', and as such, the clasp body 232' moves around the deflector 180' as the lever body 230' is moved between the secured position and the unsecured position.

In order to minimize the possibility of a user being pinched by the lever body 230', the wing portion 184' of the deflector 180' shields the opening 206' of the latch interior 204', preventing anything from passing through the opening 206'. In order to block the opening 206', the wing portion 184' extends from the hub portion 182' in a direction substantially parallel to the pivot axis 238'. The wing portion 184' is positioned on the hub portion 182' at a first angular location 210' relative to the pivot axis 238'. Said differently, the wing portion 184' is radially spaced from the pivot axis 238' and defines the first angular location 210'.

In addition to the wing portion 184', the deflector 180' comprises the tab 186'. The tab 186' is coupled to the hub portion 182' separate from the wing portion 184'. The tab 186' may engage the mount body 160' when the lever body 230' is in the unsecured position for retaining the lever body 230' in the unsecured position. The tab 186' may alternatively engage the lid when the lever body 230' is in the unsecured position for retaining the lever body 230' in the unsecured position. Similarly, the tab 186' may be disengaged from the mount body 160' when the lever body 230' is in the secured position. As such, the tab 186' may limit free movement of the lever body 230' from the unsecured position to the secured position.

Similar to above, the tab 186' limits free movement of the lever body 230', which is effected via engagement between the tab 186' and the lever body 230'. To this end, the tab 186' may be coupled to the hub portion 182' and extend toward a second angular location 212'. The second angular location 212' being spaced from the first angular location 210'. The tab 186' may be formed from a metal and comprise a fixed end 192' and a free end 194', with the fixed end 192' coupled to the hub portion 182' and the free end 194' extending therefrom. The free end 194' is spaced from the hub portion 182' such that the free end 194' is able to move relative to the hub portion 182'. The free end 194' may comprise a protrusion 196', which is able to engage the mount body recess 166' of the mount body 160' to hold the lever body 230' in the unsecured position. Moving the lever body 230' into, or out of, the unsecured position flexes the tab 186', adding resistance to the movement.

Several instances have been discussed in the foregoing description. However, the aspects discussed herein are not intended to be exhaustive or limit the disclosure to any particular form. Various modifications to these aspects will be readily apparent to those skilled in the art, and the generic principles defined herein may be applied to other aspects without departing from the scope of the disclosure. The terminology that has been used is intended to be in the nature of words of description rather than of limitation. Many modifications and variations are possible in light of the above teachings and the disclosure may be practiced otherwise than as specifically described.

CLAUSES

I. A sterilization container for medical instruments, the sterilization container comprising: a base and a lid configured for engaging the base, the base and the lid collectively defining a volume for receiving medical instruments; a latch attached to one of the base and the lid, the latch comprising: a mount body including a back portion and two side portions, wherein the back portion is coupled to the lid or the base; a lever body including two side portions, wherein the two side portions of the lever body are pivotably coupled to two side portions of the mount body such that the lever body is movable about a pivot axis between a secured position and an unsecured position, and wherein the lever body and the mount body cooperate to define an interior and further define an opening of the interior when the lever body is in the secured position; and a deflector positioned at least partially within the interior and movable with the lever body for concurrent movement about the pivot axis, the deflector comprising: a hub portion supported on the pivot axis; a wing portion extending from the hub portion to define an outer surface, wherein the outer surface is positioned adjacent to the opening of the interior when the lever body is in the secured position for preventing access to the interior through the opening; and a tab coupled to the hub portion and separate from the wing portion, the tab engages the mount body when the lever body is in the unsecured position for retaining the lever body in the unsecured position.

II. The sterilization container of clause I, wherein the tab is disengaged from the mount body when the lever body is in the secured position.
III. The sterilization container of clause I, wherein the lever body defines a link axis extending through the two side portions, and further comprising a clasp body at least partially disposed in the interior, the clasp body having an interface end selectively engageable with one of the base and the lid, and a link end, wherein the link end is rotatably supported on the link axis.
IV. The sterilization container of clause III, wherein the mount body is coupled to the lid and the clasp body is engageable with the base, and wherein the secured position of the lever body is further defined as the lever body being pivoted toward the base and the unsecured position of the lever body is further defined as the lever body being pivoted toward the lid.
V. The sterilization container of clause III, wherein the wing portion defines an arc angle greater than 75 degrees.
VI. The sterilization container of clause III, wherein the wing portion comprises a first wing portion extending from the hub portion in a first axial direction and a second wing portion extending from the hub portion in a second axial direction.
VII. The sterilization container of clause III, wherein the wing portion extends from the hub portion in a direction parallel to the pivot axis and is positioned at a first angular location.
VIII. The sterilization container of clause VII, wherein the tab is positioned at a second angular location spaced from the first angular location.
IX. The sterilization container of clause VIII, wherein the hub portion defines a first bore and a second bore, the first bore aligned with the pivot axis and the second bore radially spaced therefrom and aligned with the link axis, and wherein the second bore is positioned at a third angular location.
X. The sterilization container of clause IX, wherein the tab extends between a fixed end coupled to the hub portion and a free end spaced from the hub portion, and wherein the free end comprises a protrusion defining the second angular location.
XI. The sterilization container of clause X, wherein a first deflector radius is defined between the pivot axis and an outermost point at the first angular location and a second deflector radius is defined between the pivot axis and an outermost point of the protrusion, and wherein the second deflector radius is greater than the first deflector radius.
XII. The sterilization container of clause XI, wherein the clasp body defines an arcuate profile between the interface end and the link end, wherein a clasp offset is defined between the clasp body and the pivot axis, and wherein the clasp offset is less than the second deflector radius.
XIII The sterilization container of clause XII, wherein the clasp offset is approximately equal to the first deflector radius when the lever body is in the secured position.
XIV. The sterilization container of clause XII, wherein a pivot shaft is arranged on the pivot axis and supports the lever body and the deflector for rotation about the pivot axis, wherein the pivot shaft protrudes from the hub portion such that the pivot shaft is spaced from the clasp body when the lever body is in the secured position and as the lever body is pivoted away from the secured position the pivot shaft engages the clasp body such that further pivoting the lever body toward the unsecured position moves the interface end of the clasp body away from the base.
XV. The sterilization container of clause IX, wherein when the lever body is in the secured position the first angular location is nearer to the container than the second angular location, and when the lever body is in the unsecured position the second angular location is nearer to the container than the first angular location.
XVI. The sterilization container of clause III, wherein the clasp body comprises a first clasp portion and a second clasp portion with a pocket defined therebetween, and wherein the hub portion of the deflector is at least partially arranged in the pocket.
XVII. The sterilization container of clause XVI, wherein the wing comprises a first wing portion extending from the hub portion arranged adjacent to the first clasp portion, and a second wing portion extending from the hub portion arranged adjacent to the second clasp portion.
XVIII. The sterilization container of clause I, wherein the interior defines an interior width, and the wing portion defines a deflector width, and wherein a ratio of the deflector width to the interior width is at least 0.65.

What is claimed is:
1. A sterilization container for medical instruments, the sterilization container comprising:
a base and a lid configured for engaging the base, the base and the lid collectively defining a volume for receiving medical instruments;
a latch attached to one of the base and the lid, the latch comprising:
a mount body including a back portion and two side portions, wherein the back portion is coupled to the lid or the base;
a lever body including two side portions, wherein the two side portions of the lever body are pivotably coupled to the two side portions of the mount body such that the lever body is movable about a pivot axis between a secured position and an unsecured position, and wherein the lever body and the mount body cooperate to define an interior and further define an opening of the interior when the lever body is in the secured position; and
a deflector positioned at least partially within the interior and movable with the lever body for concurrent movement about the pivot axis, the deflector comprising:
a hub portion supported on the pivot axis;
a wing portion extending from the hub portion to define an outer surface, wherein the outer surface is positioned adjacent to the opening of the interior when the lever body is in the secured position for preventing access to the interior through the opening; and
a tab coupled to the hub portion and separate from the wing portion, wherein the tab is arranged to engage the mount body when the lever body is in the unsecured position for retaining the lever body in the unsecured position;
wherein the lever body defines a link axis extending through the two side portions, and further comprising a clasp body at least partially disposed in the interior, the clasp body having an interface end selectively engageable with the other one of the base and the lid, and a link end, wherein the link end is rotatably supported on the link axis; and wherein the wing portion comprises a first wing portion extending from the hub portion in a first axial direction and a second wing portion extending from the hub portion in a second axial direction, wherein the first wing portion and the second wing portion are configured to engage the clasp body and move to disengage the interface.

2. The sterilization container of claim 1, wherein the tab is disengaged from the mount body when the lever body is in the secured position.

3. The sterilization container of claim 1, wherein the mount body is coupled to the lid and the clasp body is engageable with the base, and wherein the secured position of the lever body is further defined as the lever body being pivoted toward the base and the unsecured position of the lever body is further defined as the lever body being pivoted toward the lid.

4. The sterilization container of claim 1, wherein the wing portion defines an arc angle greater than 75 degrees.

5. The sterilization container of claim 1, wherein the wing portion extends from the hub portion in a direction parallel to the pivot axis and is positioned at a first angular location.

6. The sterilization container of claim 5, wherein the tab is positioned at a second angular location spaced from the first angular location.

7. The sterilization container of claim 6, wherein the hub portion defines a first bore and a second bore, the first bore aligned with the pivot axis and the second bore radially spaced therefrom and aligned with the link axis, and wherein the second bore is positioned at a third angular location.

8. The sterilization container of claim 7, wherein the tab extends between a fixed end coupled to the hub portion and a free end spaced from the hub portion, and wherein the free end comprises a protrusion defining the second angular location.

9. The sterilization container of claim 8, wherein a first deflector radius is defined between the pivot axis and an outermost point at the first angular location and a second deflector radius is defined between the pivot axis and an outermost point of the protrusion, and wherein the second deflector radius is greater than the first deflector radius.

10. The sterilization container of claim 9, wherein the clasp body defines an arcuate profile between the interface end and the link end, wherein a clasp offset is defined between the clasp body and the pivot axis, and wherein the clasp offset is less than the second deflector radius.

11. The sterilization container of claim 10, wherein the clasp offset is approximately equal to the first deflector radius when the lever body is in the secured position.

12. The sterilization container of claim 10, wherein a pivot shaft is arranged on the pivot axis and supports the lever body and the deflector for rotation about the pivot axis, wherein the pivot shaft protrudes from the hub portion such that the pivot shaft is spaced from the clasp body when the lever body is in the secured position and as the lever body is pivoted away from the secured position the pivot shaft engages the clasp body such that further pivoting the lever body toward the unsecured position moves the interface end of the clasp body away from the base.

13. The sterilization container of claim 7, wherein when the lever body is in the secured position the first angular location is nearer to the lid than the second angular location, and when the lever body is in the unsecured position the second angular location is nearer to the lid than the first angular location.

14. The sterilization container of claim 1, wherein the clasp body comprises a first clasp portion and a second clasp portion with a pocket defined therebetween, and wherein the hub portion of the deflector is at least partially arranged in the pocket.

15. The sterilization container of claim 14, wherein the first wing portion extends from the hub portion and is arranged adjacent to the first clasp portion, and the second wing portion extends from the hub portion and is arranged adjacent to the second clasp portion.

16. The sterilization container of claim 1, wherein the interior defines an interior width, and the wing portion defines a deflector width, and wherein a ratio of the deflector width to the interior width is at least 0.65.

17. A latch for a sterilization container for medical instruments having a base and a lid removably engageable with the base, the latch comprising:
a mount body coupled to one of the lid and the base and including two side portions;
a lever body including two side portions, wherein each of the two side portions of the lever body are pivotably coupled to one of the two side portions of the mount body such that the lever body is movable about a pivot axis between a secured position and an unsecured position, and wherein the lever body and the mount body cooperate to define an interior and further define an opening of the interior when the lever body is in the secured position; and
a deflector supported on the pivot axis and positioned at least partially within the interior and movable with the lever body about the pivot axis, the deflector comprising:
a hub portion;
a wing portion extending from the hub portion to define an outer surface, wherein the outer surface is positioned adjacent to the opening of the interior for preventing access to the interior through the opening; and
a tab coupled to the hub portion and arranged to engage the mount body when the lever body is in the unsecured position for retaining the lever body in the unsecured position;
wherein the lever body defines a link axis extending through the two side portions, and further comprising a clasp body at least partially disposed in the interior, the clasp body having an interface end selectively engageable with the other one of the base and the lid, and a link end, wherein the link end is rotatably supported on the link axis; and
wherein the wing portion comprises a first wing portion extending from the hub portion in a first axial direction and a second wing portion extending from the hub portion in a second axial direction, wherein the first wing portion and the second wing portion are configured to engage the clasp body and move to disengage the interface.

18. A sterilization container for medical instruments, the sterilization container comprising:
a base and a lid configured for engaging the base, the base and the lid collectively defining a volume for receiving medical instruments;
a latch attached to one of the base and the lid, the latch comprising:
a mount body including a back portion and two side portions, wherein the back portion is coupled to the lid or the base;
a lever body including two side portions, wherein the two side portions of the lever body are pivotably coupled to the two side portions of the mount body such that the lever body is movable about a pivot axis between a secured position and an unsecured position, and wherein the lever body and the mount body cooperate to define an interior and further define an opening of the interior when the lever body is in the secured position; and a deflector positioned at least partially within the interior and movable with the lever body for concurrent movement about the pivot axis, the deflector comprising:

a hub portion supported on the pivot axis;

a wing portion extending from the hub portion to define an outer surface, wherein the outer surface is positioned adjacent to the opening of the interior when the lever body is in the secured position for preventing access to the interior through the opening; and a tab coupled to the hub portion and separate from the wing portion, wherein the tab is arranged to engage the mount body when the lever body is in the unsecured position for retaining the lever body in the unsecured position;

wherein the lever body defines a link axis extending through the two side portions, and further comprising a clasp body at least partially disposed in the interior, the clasp body having an interface end selectively engageable with the other one of the base and the lid, and a link end, wherein the link end is rotatably supported on the link axis; and wherein the wing portion extends from the hub portion in a direction parallel to the pivot axis and is positioned at a first angular location.

\* \* \* \* \*